United States Patent [19]

Oeser et al.

[11] 4,226,811
[45] Oct. 7, 1980

[54] PREPARATION OF SUBSTITUTED FLUOROBENZENES

[75] Inventors: Heinz-Guenter Oeser, Ludwigshafen; Karl-Heinz Koenig, Frankenthal; Dietrich Mangold, Neckargemuend, all of Fed. Rep. of Germany

[73] Assignee: BASF Aktiengesellschaft, Fed. Rep. of Germany

[21] Appl. No.: 2,596

[22] Filed: Jan. 11, 1979

[30] Foreign Application Priority Data

Jan. 26, 1978 [DE] Fed. Rep. of Germany ....... 2803259

[51] Int. Cl.³ ............................................. C07C 79/12
[52] U.S. Cl. ..................................... 568/937; 568/938
[58] Field of Search ......................................... 260/646

[56] References Cited

U.S. PATENT DOCUMENTS

| 3,064,058 | 11/1962 | Duesel et al. | 260/646 |
| 3,240,824 | 3/1966 | Boudakian et al. | 260/646 |
| 4,069,262 | 1/1978 | Kunz | 260/646 |

OTHER PUBLICATIONS

Finger et al., J. Am. Chem. Soc., vol. 78 (1956) pp. 6034 to 6036.
Starr et al., Chemistry and Industry, 1962, pp. 1328 to 1329.
Vorozhtsov et al., Chem. Abstracts, vol. 57, (1962), 9706h to 9707b.
Sam et al., J. Am. Chem. Soc., vol. 96 (1974), pp. 2250 to 2253.

Primary Examiner—Leland A. Sebastian
Attorney, Agent, or Firm—Keil & Witherspoon

[57] ABSTRACT

A process for the preparation of substituted fluorobenzenes which contain a nitro group or a cyano group and may or may not contain an aliphatic radical or an additional halogen atom, wherein the corresponding substituted chlorobenzene is reacted with potassium fluoride in the presence of a crown ether and a solvent at from 150° to 230° C.

3 Claims, No Drawings

PREPARATION OF SUBSTITUTED FLUOROBENZENES

The present invention relates to a novel process for the preparation of substituted fluorobenzenes by reaction of substituted chlorobenzenes with potassium fluoride in the presence of a crown ether and of a solvent.

Chemistry and Industry (1962), 1,328–1,329, describes the preparation of o- and p-fluoronitrobenzene by reaction of the corresponding chlorobenzenes with potassium fluoride at 221°–230° C. for 7 hours in the presence of dimethylsulfone, the yield being 60–73 percent. This publication points out that in dimethylformamide or dimethylsulfoxide the fluorination in most cases only proceeds sluggishly and the reaction is unsatisfactory. In dimethylsulfoxide, the reaction mixture undergoes decomposition, with formation of foul-smelling, sulfur-containing by-products; the reaction time is stated to be 15 hours.

J. Amer. Chem. Soc., 78 (1956), 6,034–6,036 describes the reaction of various mononitrochlorobenzenes in dimethylformamide and dimethylsulfoxide at 175°–190° C. with reaction times of from 2 to 163 hours, the yields being from 10 to 72 percent.

The reaction of 2-chloronitrobenzene in dimethylformamide gave an estimated yield of only 40 percent even if the reaction was continuous for 163 hours at 170° C.

Chemical Abstracts, 57 (1962), 9,706 h–9,707 b discloses that instead of using potassium fluoride, the reaction can also be carried out with cesium fluoride at 190°–200° C. in the absence of a solvent and with a reaction time of 25 hours; a 30–50 percent excess of cesium fluoride over the stoichiometric amount is needed. o-Fluoronitrobenzene is obtained in 80 percent yield, whilst the yield of the p-isomer is from 70 to 80 percent.

U.S. Pat. No. 3,064,058 describes a similar reaction in tetramethylenesulfone as the solvent. In order to obtain a dry reaction mixture, the process is carried out by first suspending the alkali metal fluoride in the solvent and then distilling the suspension until all the water present therein has been removed together with from 5 to 15 percent by weight of tetramethylenesulfone. p-Nitrochlorobenzene is then added to the suspension. Only sodium fluoride and potassium fluoride are mentioned as the alkali metal fluorides, and only potassium fluoride is referred to in the Examples. The Examples show that the yield of 93.5 percent is achieved at 240° C. with a reaction time of 12 hours, to which must be added the time required for the distillation.

U.S. Pat. No. 3,240,824 concludes, from the above prior art, that mononitro-o- and -p-chlorobenzene are best reacted with potassium fluoride as the sole alkali metal fluoride, in the absence of a solvent, at from 270° to 320° C. It points out that the use of cesium fluoride is too uneconomical, and that the solvents used must be recovered by involved methods which entail losses; drying the solvent-containing starting mixture is frequently difficult and requires a special fractionation technique. In the light of all the Examples, the conditions proposed in the said U.S. patent give, for reaction times of 24 hours, yields of only 56.5 percent (o-compound) or 60.6 percent (p-compound), with conversions of 50.5 percent (o-compound) or 52.5 percent (p-compound).

J. Amer. Chem. Soc., 96 (1974), 2,250–2,252 describes the reaction of 2,4-dinitrochlorobenzene with potassium fluoride in the presence of 18-crown-6 ether.

U.S. Pat. No. 4,069,262 discloses that 2-fluoronitrobenzene may be prepared from 2-chloronitrobenzene and potassium fluoride by carrying out the reaction at from 240° to 250° C. in a crown ether plus sulfolane. If the reaction is carried out at below 240° C., the yield is unsatisfactory.

We have found that a substituted fluorobenzene of the formula

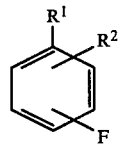

where $R^1$ is nitro or cyano and $R^2$ is hydrogen, an aliphatic radical or halogen, is obtained in an advantageous manner by reaction of a substituted chlorobenzene with potassium fluoride in the presence of a solvent, if a substituted chlorobenzene of the formula

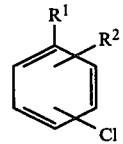

where $R^1$ and $R^2$ have the above meanings, is reacted in the presence of a crown ether and of an N,N-substituted carboxylic acid amide, nitrobenzene, a nitrile, an aliphatic sulfone and/or an aliphatic sulfoxide as the solvent, at from 150° to 230° C.

If o-chloronitrobenzene is used, the reaction may be represented by the following equation:

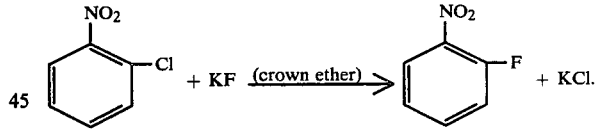

Compared to the prior art, the process according to the invention gives a very good result in respect of yield, purity of the end product, low reaction temperature and virtually complete recycling of the solvent. The yield and purity are better than in virtually all other processes. Compared to the process described in Chemical Abstracts, 57 (loc. cit.), the process according to the invention is more economical and can be carried out on an industrial scale. Compared to the process described in U.S. Pat. No. 3,064,058, simple drying of the potassium fluoride, for example for from 1.5 to 2.5 hours in a drying oven, suffices, and the involved azeotropic removal of water, entailing losses in operating time, solvent and energy, is dispensed with. This advantageous result of the process is surprising, even, for example, in the light of the reaction of 2,4-dinitrochlorobenzene with potassium fluoride in the presence of 18-crown-6 ether, described in J. Amer. Chem. Soc., 96 (1974), 2,250–2,252, since the starting materials to be used according to the invention, which contain only one nitro group, could hitherto only be converted to the corresponding fluorine compounds at very high temperatures and with moderate yields, and do not give useful results under the conditions of the prior art process, ie. at 83° C. in the presence of 18-crown-6 ether. It was not to be expected from the disclosures of U.S. Pat. No. 4,069,262 that the process according to the invention, which is carried out at 150°–230° C., would give such advantageous results.

The starting material II is reacted with potassium fluoride in the stoichiometric amount or in excess, preferably using from 1 to 5, more especially from 2 to 4.5, moles of potassium fluoride per mole of starting material II. Preferred starting materials II and accordingly preferred end products I are those where $R^1$ is nitro or cyano and $R^2$ is hydrogen or alkyl of 1 to 4 carbon atoms which may in addition be substituted by groups which are inert under the reaction conditions, eg. alkyl or alkoxy of 1 to 4 carbon atoms, or is bromine, iodine or especially fluorine. The fluorine atom of the end product I and the chlorine atom of the starting material II can be in the meta-position but are advantageously in the para-position and especially in the ortho-position to the nitro group or cyano group.

The following are examples of suitable substituted chlorobenzenes II: o-chloronitrobenzene, m-chloronitrobenzene, p-chloronitrobenzene, o-chlorobenzonitrile, m-chlorobenzonitrile, p-chlorobenzonitrile; 2-methyl-, 2-ethyl-, 2-propyl-, 2-isopropyl-, 2-butyl-, 2-isobutyl-, 2-sec.-butyl-, 2-tert.-butyl- and 2-fluoro-4-chloro-nitrobenzene, 4-methyl-, 4-ethyl-, 4-propyl-, 4-isopropyl-, 4-butyl-, 4-isobutyl-, 4-sec.-butyl-, 4-tert.-butyl- and 4-fluoro-2-chloronitrobenzene and corresponding 2-chloronitrobenzenes substituted in the 3-position, 5-position or 6-position instead of in the 4-position, as well as correspondingly substituted 2-chlorobenzonitriles and 4-chlorobenzonitriles, 3-chloronitrobenzenes and 3-chlorobenzonitriles.

Particular interest attaches to the preparation of a substituted fluorobenzene of the formula

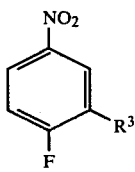

III where $R^3$ is an aliphatic radical or a halogen, from the substituted chlorobenzene of the formula

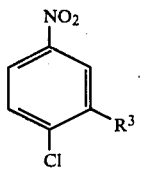

IV where $R^3$ has the above meaning. Examples of substituted chlorobenzenes of the formula IV are 3,4-dichloronitrobenzene, 3-methyl-4-chloronitrobenzene and 3-fluoro-4-chloronitrobenzene.

Examples of suitable crown ethers are 18-crown-6, 15-crown-5 and dibenzo-18-crown-6. The crown ether is advantageously used in an amount of less than 0.1, advantageously from 0.001 to 0.1, preferably from 0.003 to 0.03, especially from 0.05 to 0.025, mole per mole of starting material II. Examples of suitable solvents are N,N-disubstituted carboxylic acid amides, eg. dimethylformamide and tetramethylurea, nitrobenzene and nitriles, eg. acetonitrile and benzonitrile; preferred solvents are dimethylformamide and especially aliphatic sulfones and sulfoxides, advantageously of the formula

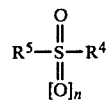

V where $R^4$ and $R^5$ are identical or different and each is an aliphatic radical, preferably alkyl of 1 to 8, especially of 1 to 4, carbon atoms, or $R^4$ and $R^5$ together are alkylene of 4 or 5 carbon atoms and n is 0 or 1. Examples of suitable solvents V are dimethylsulfoxide, diethylsulfoxide, dipropylsulfoxide, diisopropylsulfoxide, di-n-butylsulfoxide, diisobutylsulfoxide, dipentylsulfoxide, dihexylsulfoxide, diheptylsulfoxide, dioctylsulfoxide, methylethylsulfoxide, tetramethylenesulfoxide, pentamethylenesulfoxide, dimethylsulfone, diethylsulfone, dipropylsulfone, diisopropylsulfone, dibutylsulfone, diisobutylsulfone, dipentylsulfone, dihexylsulfone, diheptylsulfone, dioctylsulfone, methylethylsulfone, tetramethylenesulfone and pentamethylenesulfone; tetramethylenesulfone is particularly preferred. Solvent mixtures can also be used. Advantageously, the solvent is used in an amount of from 50 to 1,000 percent by weight, preferably from 100 to 200 percent by weight, based on starting material II.

The reaction is carried out at from 150° to 230° C., preferably from 160° to 200° C., under atmospheric or superatmospheric pressure, continuously or batchwise.

The reaction may be carried out as follows: a mixture of the starting material II, potassium fluoride, the crown ether and the solvent is kept at the reaction temperature for from 2 to 100 hours. Before the reaction, the potassium fluoride is dried in any desired manner, advantageously by a method which is simple to operate, for example in a drying chamber, or in chamber dryers, ribbon dryers or tray dryers; fluidized bed dryers, drum dryers and plate dryers may also be used. After the reaction, the end product is isolated in the conventional manner, for example by filtering, washing the solid residue and distilling the filtrate and wash filtrates.

The substituted fluorobenzenes obtainable by the process of the invention are valuable starting materials for the preparation of dyes, drugs and pesticides. For example, they may be reduced to fluoroanilines which can be used in paints, germicides or soldering fluxes. Regarding the use of the compounds, reference may be made to the above publications.

In the Examples which follow, parts are by weight.

EXAMPLE 1

1,300 parts of o-chloronitrobenzene, 960 parts of potassium fluoride and 82.5 parts of 18-crown-6 in 1,300 parts of tetramethylenesulfone are stirred under nitrogen for 30 hours at 180° C. The solution is cooled to 110° C. and filtered, the solid residue is rinsed with 500 parts of methylene chloride and the filtrates are combined and distilled. 932 parts (80% of theory) of o-fluoronitrobenzene of boiling point 55°–57° C./1.2 mm Hg and 1,290 parts (99.2% of theory) of tetramethylenesulfone of boiling point 105°–110° C. are obtained. About 70% of the crown ether can be recovered from the distillation residue by repeated extraction by shaking with water.

EXAMPLE 2

A suspension of 1,500 parts of 3,4-dichloronitrobenzene, 680 parts of potassium fluoride and 25 parts of 18-crown-6 in 1,420 parts of dimethylformamide is refluxed for 9 hours, the temperature being 165° C. The mixture is worked up by the method described in Example 1. 1,124 parts (82% of theory) of 3-chloro-4-fluoronitrobenzene of melting point 41°–42° C. are obtained.

EXAMPLE 3

1,500 parts of 3,4-dichloronitrobenzene, 680 parts of potassium fluoride and 20 parts of 18-crown-6 in 1,300 parts of tetramethylenesulfone are stirred under nitrogen for 4 hours at 180° C. The mixture is worked up by the method described in Example 1. The following are obtained:

1st fraction: boiling point 63°–65° C./0.5 mm Hg.

Yield: 1,203 g (87.8%) of 3-chloro-4-fluoronitrobenzene.

2nd fraction: boiling point 65°–100° C./0.5 mm Hg.

Yield: 80 g (40.4% of 3-chloro-4-fluoronitrobenzene, 39.8% of 3,4-dichloronitrobenzene and 19.8% of sulfolane).

3rd fraction: boiling point 100° C./0.5 mm Hg.

Yield: 1,256 g (96.6%) of sulfolane.

We claim:

1. A process for the preparation of a substituted fluorobenzene of the formula

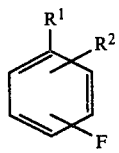

where $R^1$ is nitro or cyano and $R^2$ is hydrogen, an aliphatic radical or halogen, by reacting a substituted chlorobenzene of the formula

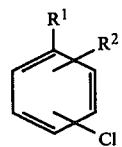

where $R^1$ and $R^2$ have the above meanings, with potassium fluoride in the presence of a crown ether and in the presence of an N,N-disubstituted carboxylic acid amide, nitrobenzene, nitrile, aliphatic sulfone and/or aliphatic sulfoxide as solvent, said reaction being carried out at from 150° to 230° C.

2. A process as claimed in claim 1, wherein the reaction is carried out at from 160° to 200° C.

3. A process as claimed in claim 1, wherein a substituted chlorobenzene of the formula

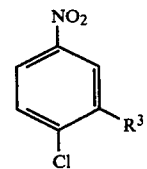

where $R^3$ is an aliphatic radical or halogen, is reacted.

* * * * *